United States Patent [19]

Schenk

[11] 4,257,406

[45] Mar. 24, 1981

[54] IRIS RETRACTOR AND PUPIL DILATOR

[76] Inventor: Alan G. Schenk, 8149 W. Ogden Ave., Apt. 6, Lyons, Ill. 60534

[21] Appl. No.: 41,002

[22] Filed: May 18, 1979

[51] Int. Cl.³ .............................................. A61B 17/02
[52] U.S. Cl. ..................................... 128/20; 128/345
[58] Field of Search ................. 128/341, 345, 20, 321, 128/354

[56] References Cited

U.S. PATENT DOCUMENTS

| 724,889 | 4/1903 | Kochenderfer | 128/345 |
| 4,143,427 | 3/1979 | Avis | 128/321 |
| 4,147,167 | 4/1979 | Hickmann et al. | 128/20 |

FOREIGN PATENT DOCUMENTS

| 36108 | 2/1906 | Switzerland | 128/345 |
| 113481 | 2/1918 | United Kingdom | 128/321 |
| 164405 | 11/1963 | U.S.S.R. | 128/354 |

Primary Examiner—John D. Yasko

[57] ABSTRACT

An instrument for use in ophthalmic surgery to retract the iris and provide optimal dilation of the pupil in a facile, atraumatic, and thoroughly controllable fashion. The instrument includes a pair of curved retracting tips adapted to engage the iris gently and positively for expanding the pupil to permit removal of the crystalline lens without injury to the iris. The retracting tips are mounted on a pair of cross-action spring arms and the instrument is designed for easy comfortable one-hand operation.

8 Claims, 6 Drawing Figures

4,257,406

IRIS RETRACTOR AND PUPIL DILATOR

BACKGROUND OF THE INVENTION

1. Field of the Invention

This invention relates generally to the field of surgery and more particularly to iris retracting instruments for use in ophthalmic surgery.

2. Description of the Prior Art

A number of instruments have been developed for use as iris retractors in ophthalmic surgery. These instruments generally are identified by the name of their developer and are commercially available. These include the iris retractors of Spivey, Bronson-Turtz, Rosenbaum-Drews, and Rizzuti. All of the above identified instruments are unitary hook or blade-type structures.

Such devices frequently have a number of disadvantages; for one, retraction of the iris is along one vector only, secondly they are frequently difficult to insert and remove; thirdly, they are generally unable to alter the attained pupillary size under different operative conditions; fourthly, they are generally unable to place simultaneous pressure during iris retraction on the posterior edge of the corneal wound to aid in expression of the lens; and fifthly, application at specific points of excessive force on the iris sphincter can damage this structure.

Another instrument designed for this purpose is the Eisner speculum. This speculum includes a pair of relatively large curved blades mounted on a tweezers-like structure that is outwardly spring-biased. The curved tips do not provide adequate positively engaging surfaces for engaging the iris nor is the outward movement or expansion of the tips limited except by the manipulation of the operator and the outermost spring expansion limit. The size of Eisner's tips or blades do not permit easy insertion into the pupil and they lack adequate iris grasping capability. The fact that the blades of Eisner fail to have a lower lip for engaging the iris requires that the surgeon maintain pressure with the instrument on the anterior surface of the lens. If this downward pressure is relaxed temporarily, one or more of the blades can be disengaged and the pupil collapsed at a critical time. In addition, Eisner's retracting blades have discrete front and back edges which can cause excess force to be exerted at discrete points on the iris sphincter and to cause injury at these points. The design of Eisner's handle makes it necessary for the surgeon to manipulate the instrument with his hand held in an uncomfortable and awkward mid-line position. In manipulating Eisner's instrument, the separation of the blades is achieved by relaxation of the grip pressure on the handle. Relaxation of this pressure also loosens the operator's grip on the instrument and makes precise manipulation difficult. The design of Eisner's blades prohibits the application of pressure on the posterior lip of the corneal incision so that pressure cannot be simultaneously exerted to facilitate lens expression and extraction. An instrument similar to the Eisner speculum but designed for use in performing spinal fusion is the Spreader Instrument of Peterson shown in Pat. No. 3,916,907.

A number of other instruments for use in eye surgery have also been described in the patent art. These include the patent to Suffa entitled "Speculum" U.S. Pat. No. 1,237,121 and the patent to Pulliam entitled "Eye Speculum" U.S. Pat. No. 2,438,646. Both of these inventions are intended to be used for separating the eye lids of a patient and are not designed for retraction of the iris.

Additional patents specifically designed for use in iris retraction are the Surgical Device of Illig. U.S. Pat. No. 3,490,455 and the Ocular Surgical System of McReynolds, U.S. Pat. No. 4,037,589. The device of Illig is an iris engaging hook 12 and is designed to be sutured to the sclera of the eye. A considerable amount of time is involved in the placement and removal of the devices of Illig and, if used in conjunction with crystalline lens removal, may permit the escape of vitreous humor through the pupil because of the time delay involved in its removal from the eye.

The system of McReynolds employs a speculum frame for maintaining the eyelids apart and a plurality of wire hooks which engage the iris to separate the iris outwardly. As was true for the Illig device, the placement and removal of the hooks require an undue amount of time operative risk.

SUMMARY OF THE INVENTION

It is an object of the present invention to provide an improved ophthalmic instrument which permits the ophthalmic surgeon to retract and dilate the iris of a patient in a comfortable and thoroughly controllable fashion. The instrument provides optimal dilation of the pupil in order that the crystalline lens of the patient can be engaged readily and without injury to the iris. The device further permits the application of varying degrees of pressure simultaneously on the posterior edge of the corneal incision thereby forming a pupil of the most desired shape and size for permitting lens removal therethrough.

It is a more particular object to provide an ophthalmic instrument in the general form of a cross-action type of tweezers carrying a pair of iris retracting tips on its forward most limits. The device has two handles which are compressed together for separating the iris retracting tips and thereby retracting the iris and dilating the iris. The device also includes an adjustable stop mechanism disposed between the handles for adjusting the maximum limit of separation of the iris retracting tips.

The retracting tips are generally lunar shaped and are progressively curved in cross-section for sequentially engaging and expanding the margin of the iris.

BRIEF DESCRIPTION OF THE PREFERRED EMBODIMENT

Figure 1:
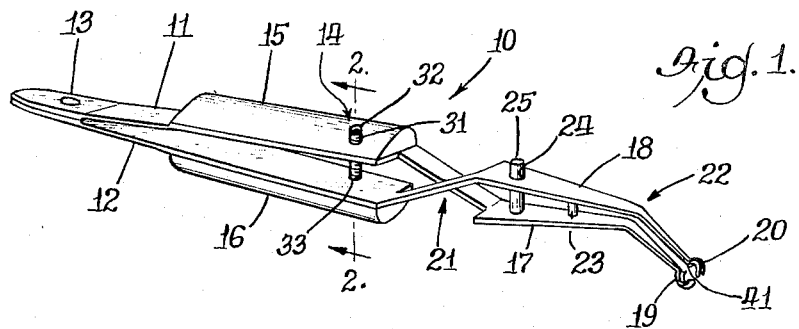
FIG. 1 is a perspective view of the improved iris retractor of the present invention.

The iris retractor of the present invention is illustrated in FIG. 1 and designated generally by the numeral 10. The retractor 10 comprises a pair of elongated leaf spring members 11 and 12 which are joined at 13 to form a unitary structure. An adjustable stop mechanism 14 is mounted between the spring members 11 and 12. Knurled eccentric handle portions 15 and 16 are mounted on the outer surfaces of the spring members 11 and 12, respectively. Elongated extensions 17 and 18 of the spring members 11 and 12, respectively, each carry an iris retracting tip 19 and 20, respectively at their outermost limits. The extensions 17 and 18 form a cross-action mechanism at 21 and are curved at 22 to permit easy insertion of the retracting tips into the eye of a patient. The tips 19 and 20 have a low profile relative to and perpendicular to the margin of the iris. A fixed stop 23 is mounted on one of the extensions 17 or 18 and abuts against the other extension and prevents the retracting tips 19 and 20 from forcefully coming into contact with each other. The upper extension 18 is formed with a circular aperture at 24 and an aligning pin 25 is mounted on and perpendicular to the extension 17 and extends longitudinally through the aperture 24.

Figure 2:
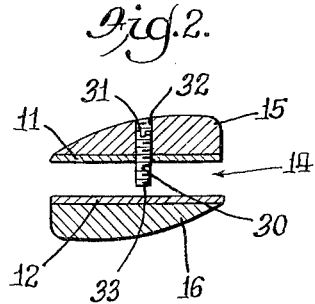
FIG. 2 is an enlarged perspective view of the adjustable stop mechanism for the instrument of FIG. 1.

The handles 15 and 16 are eccentrically curved as shown in FIG. 1 and FIG. 2 and are formed with a knurled outer surface to permit easy engagement by the manipulating hand. The eccentric curvature of each of the handles of 15 and 16 is such that the center of curvature is displaced substantially off-center of a plane perpendicular to the long axis of each spring member 11 and 12, and for each member in a direction opposite to that of the other member. This configuration permits the grasping hand to provide an obliquely oriented squeezing force to the instrument without the surgeon's hand or body being uncomfortably positioned. The aligning pin 25 maintains accurate alignment of the retracting tips 19 and 20 despite oblique forces exerted on the handle surfaces.

The adjustable stop mechanism 14 is illustrated in greater detail in Fig. 2. The stop 14 comprises a machine screw 30 formed with a slotted head 31 threaded through an aperture 32. The screw 30 is formed with fine gauge threads on its exterior and is mounted within the correspondingly threaded bore 32 formed in the handle 11.

Figure 3:
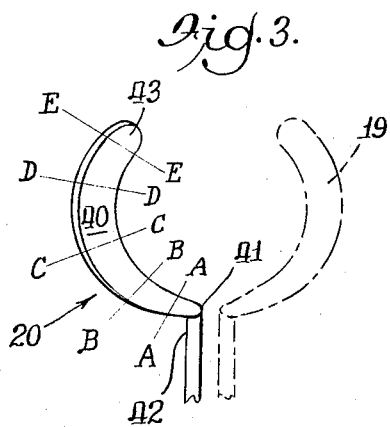
FIG. 3 is an enlarged plan view of the iris retracting tips carried by the instrument of FIG. 1.
Figure 4:
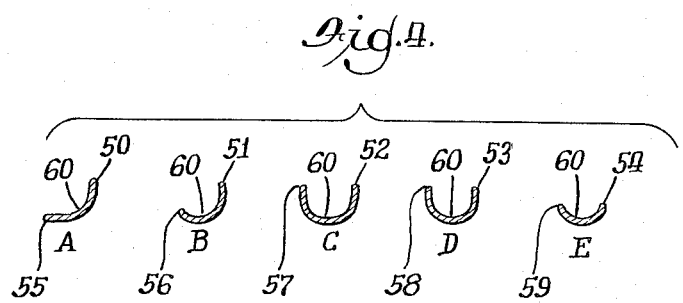
FIGS. 4A, B, C, D and E are cross-sectional views of one of the retracting tips taken on lines A—A, B—B, C—C, D—D, and E—E of FIG. 3.

The outward expansion of the retracting tips 19 and 20 is controlled and limited by the adjustment of the screw 30 of stop mechanism 14. This outward limit is established by the compression of the leaf spring 12 against the end 33 of the screw 30. Referring now to FIGS. 3 and 4, the retracting tips 19 and 20 are illustrated in greater detail. The cross-sectional views taken in FIG. 3 and shown in FIG. 4 are illustrated only for the tip 20, although it is to be understood that the retracting tip 19 is a mirror image of the tip 20. The retracting tip 20 comprises a unitary body portion 40 that may be defined in terms of primary and secondary curves. The primary curve is generally in the form of an outwardly convex lunar shaped arc of gradually decreasing radii of curvature from its point of attachment to the handle extension 18. The lunar arc corresponds generally to the configuration which the pupillary margin will take upon retraction of the iris. The rearmost aspect 41 of the body portion 40 is attached to the narrowed end of the extension 18 and a tangent to the primary curve at that point is perpendicular to a midline plane of the instrument and is also precisely aligned with the other retracting tip 19. The lower surface of the extension 18 defines a heel 42 adapted to contact the posterior lip of a corneal incision. The most forward aspect 43 of the primary curve of the body 40 has the greatest curvature. This variable curvature assures that no concentration of the dilating forces on the iris is asserted by the tips 19 and 20 might occur despite differences in the possible maximal dilations as established by the adjustable stop mechanism 14.

The secondary curves defining the configuration of the tip 20 are generally concave and perpendicular to the primary curve as illustrated in greater detail in FIG. 4. The sectional views are taken along lines A—A, B—B, C—C, D—D, and E—E of FIG. 3. the sectional views are shown to progress from a generally reversed L configuration at A to a U configuration at C and D and to a shallow U configuration at E. The sectional views may be defined in terms of upper lid indicia as shown at 50, 51, 52, 53, and 54 for the views A through E respectively. Similarly, the lower lips may be defined by indicia 55, 56, 57, 58, and 59 respectively for the corresponding sections. The upper lip indicia 50–54 are those portions which curve above the pupillary margin during use of the instrument and the lower lip portions 55–59 are those which curve beneath and under the pupillary margin. A generally concave iris contacting surface 60 is defined between the upper and lower lips. A virtual absence of a lower lip at 55 and 56 of the sections A and B respectively, allows for ease of insertion and removal of the instrument and for engaging the pupillary margin as will be described hereinafter.

In operation, the instrument 10 shown in FIG. 1 is designed for left hand operation, and would be a mirror image of a corresponding right handed model (not shown). The handles 15 and 16 are grasped and minipulated with the left hand and the operation may be understood most clearly by reference to the illustrations shown in FIGs. 5A and 5B.

Figure 5A:
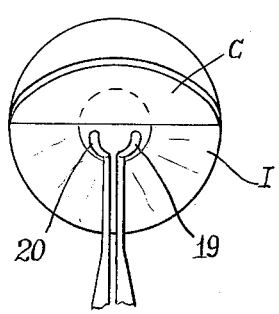
FIG. 5A is a view of the iris retracting tips as intended to be used to engage the iris of a patient.
Figure 5B:
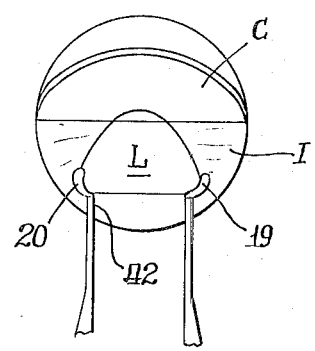
FIG. 5B is a view of the iris fully retracted and dilated.

After the cornea C has been incised and folded back upon itself as shown in FIG. 5A, the retracting tips 19 and 20 are introduced into the pupil of the iris I. A gentle downward pressure and slight backward tilting of the instrument 10 causes the lower lips 55 and 56 to engage the margin of the iris mid-line which then comes to be positioned beneath the upper lips 50 and 51 (and corresponding lips for the tip 19). The engagement of the margin of the iris which is now just off mid-line, and by virtue of the supple structure of the iris itself, guides and produces a natural rolling tendency of the iris I. The margin of the iris engaged by the surface 60 follows the mid-line, as does the remainder of the pupillary margin, so that the iris once started in effect rolls itself over the lower lips 55 and 56 of the tip 20 and in essence is captured and positions itself between the upper and lower lips. The instrument is then drawn backwards toward the surgeon at the same time squeezing pressure is applied to the handles 15 and 16 causing the retracting tips 19 and 20 to separate from each other. The pupil is then dilated as shown in FIG. 5B to a degree predetermined by the adjustable stop 14. The iris I retracted backwards as shown in FIG. 5B provides optimal exposure of the underlying lens L. During removal of the lens L through the dilated pupil, optimal pressure is simultaneously exerted by the heel 42 of the instrument on the posterior edge of the wound so as to depress the wound edge and cause the wound to gape. This slight positive pressure on the eye also facilitates lens expression and extration. Following extraction of the lens, removal of the instrument 10 is accomplished in a manner reversed to that of its insertion. Pressure on the posterior edge of the wound is relieved, the instrument is advanced forwardly away from the surgeon, and at the same time relaxing of the squeezing pressure on the handles 15 and 16 allows the tips 19 and 20 to come together. The instrument 10 is then tilted slightly forwardly to allow the iris to roll off the lower lips of the tips 19 and 20 and become disengaged therefrom.

In summary, the instrument 10 permits the ophthalmic surgeon to retract the iris I in a manner which causes the least trauma to the iris. In addition, because of the optimal retraction, the greatest protection to the iris is afforded from other instruments used to extract the lens. The construction of the handles 15 and 16, with their eccentrically curved surfaces, permits the operator to exert squeezing forces which are comfortable and normal to the hand. The aligning pin 25 retins precise alignment of the members 17 and 18 despite the obliquity of those forces. The cross-action mechanism 21 in conjunction with the two dilating tips 19 and 20 allows a firmer and more controlled grasp of the instrument 10 than can be had with instruments such as Eisner's speculum. The adjustable stop mechanism 14 permits the individual surgeon to pre-set that amount of attainable dilation which he or she believes will be safe without causing overextension of the iris sphincter or other trauma to the iris I. The heel 42 of the instrument 10 allows pressure to be placed on the posterior edge of the wound during retraction of the iris I. This pressure causes the wound to gape and provides positive vitreous pressure as needed to aid in the expression and extraction of the lens L.

The design of the retracting tips 19 and 20, particularly because of their secondary curve configuration, allows for easy insertion into the pupil as well as withdrawal from the pupil but does otherwise engage the iris positively during retractions and dilations. The low profile of the retracting tips 19 and 20 perpendicular to their plane of separation permits insertion of the instrument into a pupil of small size without the need to forcefully fold the cornea back upon itself excessively. In addition, the retracting tips 19 and 20, because of the design of their primary curve, place no undue force at any one point on the pupillary margin and thereby avoids trauma to the iris sphincter. The continuously variable degree of separation of the tips 19 and 20, limited only by the fixed stop 23 and adjustable stop 14, permits the surgeon to vary continuously, as needed, the degree of separation as is deemed optimal from moment to moment during the procedure.

The embodiment of the invention shown and described is the preferred one but it is to be understood that any one or several of the features described might be changed without departing from the spirit of the invention. For example, the instrument could be constructed with flat surfaced handles instead of the eccentric handles described so that the instrument could be used in either hand. Similarly, the cross-action mechanism could be omitted and the separation of retraction tips accomplished by spring bias by the member itself. However, as explained above, such mode of operation is not preferred, but could be employed without detracting from the utilitarian function of the retracting tips 19 and 20.

It is to be understood that the embodiment of the invention shown and described is by way of example only and many changes may be made thereto without departing from the spirit of the invention. The invention is not to be considered as limited to the embodiment shown except insofar as the claims may be so limited.

I claim:

1. An instrument adapted for use in ophthalmic surgery comprising:
   a pair of outwardly convex curved iris retracting and pupil dilating tips adapted to be mutually separated in a plane defining a plane of motion;
   curved lip means formed on upper and lower edges of each of said tips and joined by an inwardly concave external surface adapted to capture and retain the margin of an iris lying within said defined plane as said tips are increasingly separated and retracted; and
   handle means attached to said tips for effecting mutual separation thereof.

2. The instrument of claim 1 wherein:
   each of said tips comprises an outwardly convex curved body portion having radii of curvature lying in said defined plane and characterized by progressively decreasing radii from a point of attachment on said handle means to an outermost remote point.

3. The instrument of claim 1 wherein:
   said concave surface lies generally perpendicular to said defined plane and extends along an outer periphery of said curved tips.

4. The instrument of claim 3 wherein:
   said lower lip means are diminished adjacent the point of attachment to said handle means to facilitate ease of insertion of said lower lips into the pupil of an eye and removal therefrom.

5. The instrument of claim 4 wherein:
   said lower lip means gradually increase in dimension at distances more remote from said point of attachment attaining a dimension substantially equivalent to that of said upper lip means, whereby the pupillary margin of a eye is increasingly engaged for retraction.

6. The instrument of claim 4 wherein:
   said concave surfaces on each tip adjacent said point of attachment lie substantially on a common tangent in said plane of motion when said tips are at their point of minimum separation so as to minimize point of contact forces on the pupillary margin during dilation.

7. The instrument of claim 1 including:
   adjustable stop means mounted on said handle means and operable to adjust and limit the separation of said tips.

8. The instrument of claim 1 wherein:
   said handle means includes a separate handle for each tip with each handle having longitudinal dimension and significantly curved outer surfaces transverse to said longitudinal dimension with radii of curvature generally perpendicular to said longitudinal dimension, and with centers of curvature of each handle laterally displaced in a direction opposite to that of the other handle.

* * * * *